United States Patent
Matano

(10) Patent No.: US 7,160,714 B2
(45) Date of Patent: Jan. 9, 2007

(54) VEGETABLE FIBER-DIGESTING AGENT AND METHOD OF PROCESSING VEGETABLE WASTE BY USING THE SAME

(75) Inventor: Yutaka Matano, Iwakura (JP)

(73) Assignee: Menicon Co., Ltd., Nagoya (JP)

( * ) Notice: Subject to any disclaimer, the term of this patent is extended or adjusted under 35 U.S.C. 154(b) by 140 days.

(21) Appl. No.: 10/433,616

(22) PCT Filed: Dec. 28, 2001

(86) PCT No.: PCT/JP01/11619

§ 371 (c)(1),
(2), (4) Date: Jun. 17, 2003

(87) PCT Pub. No.: WO02/055686

PCT Pub. Date: Jul. 18, 2002

(65) Prior Publication Data

US 2004/0033290 A1  Feb. 19, 2004

(30) Foreign Application Priority Data

Jan. 10, 2001  (JP)  ............... 2001-002827

(51) Int. Cl.
 *C02F 3/34*  (2006.01)
 *C07G 17/00*  (2006.01)
(52) U.S. Cl. ............... 435/262; 435/267; 435/277; 47/58.1 SC; 47/905; 71/11; 71/903
(58) Field of Classification Search ............... 435/264, 435/267, 277, 278, 279, 842; 71/23, 11, 71/903; 47/1.43, 57.7, 58.1 SC, 905
See application file for complete search history.

(56) References Cited

U.S. PATENT DOCUMENTS

| | | | |
|---|---|---|---|
| 4,337,077 A * | 6/1982 | Rutherford | 71/9 |
| 4,506,010 A * | 3/1985 | Goodman et al. | 435/32 |
| 5,733,355 A * | 3/1998 | Hibino et al. | 71/6 |
| 5,759,845 A * | 6/1998 | Yu | 435/277 |
| 5,871,730 A * | 2/1999 | Brzezinski et al. | 424/94.61 |
| 5,981,233 A * | 11/1999 | Ringpfeil | 435/71.1 |
| 6,617,150 B1 * | 9/2003 | Hince | 435/262.5 |

FOREIGN PATENT DOCUMENTS

| | | |
|---|---|---|
| JP | 56-124393 | 9/1981 |
| JP | 59-159780 | 9/1984 |
| JP | 62-175178 | 7/1987 |
| JP | 2-46293 | 2/1990 |
| JP | 2-261384 | 10/1990 |
| JP | 31710997 | 8/2005 |

OTHER PUBLICATIONS

Poulsen, O.M. et al., Degradation of Microcrystalline Cellulose: Syergism between Differenct Endoglucanases of Cellulomonas sp. ATCC 21399, Biotechnology and Bioengineering, vol. 39, pp. 121-123 (1992).*

O. M. Poulsen et al.; *Degradation of Microcrystalline Cellulose: Synergism between Different Endoglucanases of Cellulomoas sp. ATCC 21399*; Biotechnology and Bioengineering, vol. 29, pp. 121-123 (1992).

R. Lamed et al.; *Efficient Cellulose Solubilization by a Combined Cellulosome-β-Glucosidase System*; Applied Biochemistry and Biotechnology; vol. 27, pp. 173-183 (1991).

Han, Y.W., et al.; "Isolation and Characterization of a Cellulose-utilizing Bacterium;" *Applied Microbiology*; vol. 16, No. 8, pp. 1140-1145 (Aug. 1968).

A copy a page from the Web site of ATCC relaing to Cellulomonas sp. ATC21399.

* cited by examiner

*Primary Examiner*—David Redding
(74) *Attorney, Agent, or Firm*—Armstrong, Kratz, Quintos, Hanson & Brooks, LLP

(57) ABSTRACT

It is an object of the present invention to provide a process for decomposing vegetable waste materials easily, which solves problems such as the problem of treatment costs, the problem of energy, an environmental problem and the problem of time for treatment which are difficult to be solved by prior art.

The present invention provides an agent for decomposing plant fibrous materials, which contains plant fibrous materials decomposing enzymes derived from a microorganism, but not the microorganism. In addition, the present invention provides a process for treating vegetable waste materials comprising allowing the agent for decomposing plant fibrous materials to act on vegetable waste materials.

5 Claims, No Drawings

VEGETABLE FIBER-DIGESTING AGENT AND METHOD OF PROCESSING VEGETABLE WASTE BY USING THE SAME

TECHNICAL FIELD

The present invention relates to an agent for decomposing plant fibrous materials and a process for treating vegetable waste materials. Specifically, the present invention relates to a process for treating of vegetable waste materials such as rice straw and chaff by using plant fibrous materials decomposing enzymes obtained from aerobic bacteria *Cellulomonas*, anaerobic bacteria *Clostridium* and/or any other microorganisms which can produce plant fibrous materials decomposing enzymes.

BACKGROUND ART

As a process for treating waste materials comprising botanical tissues generated during rice growing, a wheat production, production of grain such as corn and sugarcane, or production of legumes, adopted has been a process wherein waste materials are incinerated in the fields; a process wherein waste materials are incinerated in an incinerator with fuel such as heavy oil or light oil; or a process wherein compost is prepared by mixing vegetable waste materials with sawdust, rice bran or the like and piling the resultant up. However, the process wherein waste materials are incinerated in an incinerator requires a large quantity of fuel and the cost of transportation, and it has been considered whether the process wherein waste materials are incinerated in the fields should be prohibited, because of a problem of environmental pollution caused by the generated soot and smoke (a rice-straw pollution). Concerning the process of composting vegetable waste materials, adopted have been a process comprising mixing straw, sawdust, rice bran or the like to vegetable waste materials, sprinkling the mixture with slaked lime, piling the resulting mixture up out in the open and thereby letting it decay naturally; and a process for preparing compost comprising mixing finely-crushed vegetable waste materials with sawdust, chaff, chicken droppings or the like, regulating moisture of the mixture, adding fermentative bacteria, treated compost or the like to the resultant and stirring the resulting mixture in a container and whereby fermentation is carried out. However, according as agriculture is modernized and mechanized, the process for preparing compost tends not to be performed because of both labor and a period of time required to make the mixture ripe. Therefore, such waste materials tend to become industrial waste though it is recognized as beneficial resources.

As a process other than those mentioned above, there is a process wherein vegetable waste materials are treated with microbiological preparation. Vegetable waste materials are difficult to dissolve because of the structure, which is caused mainly by cellulose and/or hemicellulose in the vegetable waste materials. Because of this, cellulose and/or hemicellulose need to be hydrolyzed at least partly at the first step so that the plant fibrous materials can be treated and then used beneficially. As a process for hydrolyzing cellulose and/or hemicellulose, known is a process for treating wherein agents for decomposing rice straw or the like comprising the mixture of many kinds of bacteria are used. In Japanese Unexamined Patent Publication No. 157285/1996, described is a process for preparing liquid compost from vegetable waste materials wherein at least one of pectin, cellulose and hemicellulose is decomposed with plant fibrous materials decomposing enzymes produced by fungi or bacteria. However, the process requires that a place for treatment should be obtained and provided with facilities for the treatment, so that labor to transport vegetable waste materials to the place is required. Furthermore, in Japanese Unexamined Patent Publication No. 2613/1995, described is a bacterial preparation for agriculture which is sprinkled directly to the fields. However, the decomposition of vegetable waste materials by using the agent takes a long time from sprinkling of the agent over the fields to observing the effect, especially to the resulting vegetable waste materials becoming ripe. The reason is that the vegetable waste materials are decomposed with plant fibrous materials decomposing enzymes which microorganisms produce after cultivation, i.e. that the decomposition of vegetable waste materials requires the multiplication of the bacteria in soil.

For the purpose of allowing the existing bacterial preparation and lime-nitrogen agents to work effectively in cold districts such as Tohoku and Hokkaido which are in a Japanese grain-growing district, it is insufficient to plow the agents in the fields once, so that it is necessary to do that twice. At the time of rice growing, waste materials which are not decomposed ferment after rice planting to generate gas, and whereby taking root of young plant and growth of the roots are inhibited.

It is an object of the present invention to provide a process for decomposing vegetable waste materials which solves problems such as the problem of treatment costs mentioned above, the problem of energy, an environmental problem and the problem of time for treatment which are difficult to be solved by prior art, without depending on living conditions of microorganisms and without the need to transport waste materials comprising plant fibrous materials.

DISCLOSURE OF INVENTION

The present invention provides an agent for decomposing plant fibrous materials which does not contain microorganisms but plant fibrous materials decomposing enzymes derived from microorganisms and a process for treating vegetable waste materials which comprises allowing the agent for decomposing plant fibrous materials to act on vegetable waste materials, and whereby the problems mentioned above can be solved.

An agent for decomposing plant fibrous materials of the invention can be obtained according to the embodiment of the invention described as follows. In addition, a process for treating vegetable waste materials of the present invention can be carried out according to the following embodiment of the present invention. The present invention is explained in detail hereinafter.

BEST MODE FOR CARRYING OUT THE INVENTION

The term "plant fibrous materials decomposing enzymes" as used herein are enzymes derived from microorganisms which act on plant fibrous materials to decompose them in soil. Examples of plant fibrous materials decomposing enzymes are cellulase, xylase, pectinase, xylanase, pullulanase and glucosidase. The term "microorganism" as used herein is not limited as long as the microorganism produces any plant fibrous materials decomposing enzymes, and a microorganism which produces at least cellulase and/or xylanase is preferred. Example of microorganism is a microorganisms which belongs to a genus such as *Cellulomonas, Bacillus, Cellvibrio, Pseudomonas, Sporocytophaga, Ace-*

*tivibrio, Clostridium, Bacterioides, Butyrivibrio, Treponema, Ruminococcus, Streptomyces, Thermoactinomyces, Thermonospola, Chaetomium, Humicola, Myceliophthola, Sporotrichum, Talaromyces, Thermoascus, Thielavia, Acremonium, Agricus, Alternaria, Aspergillus, Botryodiplodia, Fusarium, Irpex, Myrothecium, Neurospora, Pellicularia, Penicillium, Pestalotiopsis, Pleurotus, Polyporus, Poria, pycnoporus, Pyricularia, Rhizopus, Schizophyllum, Sclerotium, Scytalidium, Termitomyces, Trametes or Trichoderma*, and produces plant fibrous materials decomposing enzymes. Among such microorganisms, plant fibrous materials decomposing enzymes derived from a microorganism which belongs to *Cellulomonas* or *Clostridium* are preferred, and plant fibrous materials decomposing enzymes derived from *Cellulomonas* are more preferred. Concrete examples of preferable species are *Cellulomonas* sp. K32A (National Institute of Bioscience and Human-Technology Agency of Industrial Science and Technology, accession number FERM BP-6766) strain and *Clostridium cellulovorans* ATCC 35296 strain. Because plant fibrous materials decomposing enzymes are allowed to work in the fields, the plant fibrous materials decomposing enzymes derived from mesophile are preferred. The term "mesophile" used herein is a microorganism which can not grow at both a high temperature range (at least 55° C.) and a low temperature range (at most 0° C.). Cellulase or xylanase activity can be measured by an usual method (Walfgang, H., Analytical Biochem., 164, 72–77, 1987; Wood, T. M. et al., Methods of Enzymology, 160, 87–112, 1988), so that a person skilled in the art can choose proper microorganisms which produce plant fibrous materials decomposing enzymes. Furthermore, as plant fibrous materials decomposing enzymes used herein, included are enzymes obtained by preparing transformant such as the microorganisms or culture cells containing a plant fibrous materials decomposing enzyme gene derived from a microorganism on the basis of gene-recombinant technique, and then cultivating the transformant.

In plant fibrous materials decomposing enzymes, there are exo-type enzymes which decompose plant fibrous materials from end thereof and endo-type enzymes which decompose fibrous materials from interior thereof. Both of them are preferred in the present invention. As a plant fibrous materials decomposing enzymes used in the present invention, preferred is an enzyme having the enzymatic activity at 10° C. to 60° C., preferably at 15° C. to 55° C. A person skilled in the art can measure enzymatic activities by using a well known method. For example, enzymatic activity of plant fibrous materials decomposing enzymes such as cellulase or xylase, endoglucanase and xylanase activities can be measured by the usual method mentioned above (Walfgang, H., 1987, Analitical Biochem., 164, 72–77; Wood, T. M. et al., Methods of Enzymology, 160, 87–112, 1988).

The term "agent for decomposing plant fibrous materials" used herein means an agent containing the plant fibrous materials decomposing enzymes described above, and an agent containing at least cellulase and/or xylanase is preferred. The formulation of an agent for decomposing plant fibrous materials is not particularly limited. Examples of formulation are liquid, powders and granules and the like. In addition, preferred is the agent for decomposing plant fibrous materials which contains both endo- and exo-types described above. An agent for decomposing plant fibrous materials can be obtained by cultivating microorganisms which produce the plant fibrous materials decomposing enzymes described above. Cultivation of microorganisms is performed by using proper medium under proper condition for each microorganism. These medium and culture condition can be selected and set appropriately by a person skilled in the art. As a source of carbon for medium, for example, used can be every kinds of fibrous materials such as filter paper, cellulose powder or the like. As a source of nitrogen, used can be ammonium salt such as ammonium sulfate, ammonium nitrate, ammonium acetate or the like; nitrate; and organic substance such as peptone, meat extract, corn steep liquor, corn gluten meal, cotton seed oil, defatted soybean or the like. Furthermore, a small amount of inorganic metals, vitamins, growth factors, for example yeast extract containing thiamine and biotin, may be added. These medium ingredients are available as long as each concentration of them does not inhibit the growth of microorganisms. It is appropriate that a source of carbon is used generally at 0.025% to 0.5% by weight. It is appropriate that a source of nitrogen is used at 0.05% to 1% by weight. Medium is generally adjusted to pH 6.5 to 8.5, and the resulting medium is sterilized to be used. A temperature range of cultivation is available as long as microorganisms can grow, and it can be appropriately determined by a person skilled in the art. In the case of aerobic microorganism, for example, liquid cultivation can be performed by general shake culture or airation cultivation using medium described above. In the case of anaerobic bacteria, liquid cultivation is performed by a general method, for example, which comprises adding a proper concentration of reductant to medium described above to keep a low oxidation-reduction potential, and then shaking culture with the resulting medium at 20° C. to 40° C. for 24 hours to a week. As a reductant, 0.03% to 0.05% of L-cysteine hydrochloride, 0.01% to 0.2% of sodium thioglycolate, 0.001% of sodium formaldehydesulfoxylate or 0.1% of ascorbic acid can be used. To obtain enzymes, cultivation is performed until the thing used as a source of carbon for medium such as broken filter paper, for example, disappears.

After cultivation, a supernatant of the culture is obtained, or a crude enzyme solution is obtained by centrifuging or filtering the supernatant of the culture. Then, the supernatant or the crude enzyme solution can be used as an agent for decomposing plant fibrous materials of the present invention. Alternatively, the supernatant may be concentrated by ultrafiltration, or it may be pulverized to the powder of the crude enzymes by a general method such as salting out with ammonium sulfate, solvent precipitaion, dialysis or freeze-drying method. Also, as an agent for decomposing plant fibrous materials, used can be a purified enzyme solution obtained by adding cellulose such as avicel to a crude enzyme solution, allowing a fraction showing cellulase activity or the like to be adsorbed thereto, and then eluting the adsorbed ingredients.

The term "vegetable waste materials" as used herein refers to waste materials generated during rice growing or a wheat production, or in producing grain such as corn and sugarcane, or in producing legumes or potatoes, and contains plant fibrous materials. Specifically, examples of vegetable waste materials are rice straw, chaff, straw, bagasse (strained sugarcane lees, core of corn) and vine of potato, and fallen leaves and chips of wood.

"A process for treating of vegetable waste materials" used herein is not limited as long as the above agent for decomposing plant fibrous materials is employed. For example, the process can be performed outside by scattering an agent for decomposing plant fibrous materials directly over vegetable waste materials left in the field. From the viewpoint that an agent for decomposing plant fibrous materials is allowed to act efficiently, it is preferable to crush vegetable waste materials into pieces before the agent is allowed to act on it.

As a way to crush vegetable waste materials into pieces, available is, for example, the way wherein rice straw or the like is harvested and cut with a combine, the way wherein tree is cut with a chain saw, the way wherein a crushing equipment to break a tree into chips is used, or the way wherein vegetable waste materials are cut or smashed with an equipment having a smashing tool or a shearing blade. In addition, it is preferable that treatment of vegetable waste materials is performed under the temperature condition of 20° C. to 50° C. It is preferable that when an agent for decomposing plant fibrous materials of the present invention is used in a greenhouse wherein greenhouse cultivation or the like is carried out, the room temperature is raised to 40° C. to 50° C. In a general field which exists outside, an agent to be plowed in soil, manure, fertilizer, compost and/or a soil conditioner such as a bacterial preparation available on the market, a lime-nitrogen agent or the like may be used at the same time.

The present invention is described and explained by means of the following Examples, but it is to be understood that the invention is not limited to only these Examples.

EXAMPLE 1

Fifty milliliters of L-Broth (5 g/l yeast extract, 10 g/l peptone, 5 g/l sodium chloride) was used for pre-cultivation of *Cellulomonas* sp. K32A. A single colony of K32A was inoculated into the pre-culture medium, and then the pre-cultivation was carried out by shake culture (250 rpm, the amplitude of 10 mm) at 37° C. overnight in a gyratory shaker (trade name: G10 Gyrotory shaker, made by New Brunswick scientific) to obtain the resulting pre-culture solution. Then, 250 ml of ⅕ PTY culture medium (1 g/l yeast extract, 1 g/l tryptone, 1 g/l peptone) added avicel (trade mark) at 0.05% was used as a culture medium, and the pre-culture solution was inoculated at 1% into the culture medium, and then cultivation was carried out by shake culture (250 rpm, the amplitude of 10 mm) at 37° C. until the substrate, i.e. avicel, disappeared (about 72 hours). After the cultivation, the resulting supernatant of the culture was obtained by centrifugation (6000 rpm, 10 minutes). The supernatant was then sterilized by filtering it, and proteins in the supernatant were precipitated by adding ammonium sulfate to saturation (80%). The precipitated proteins were dissolved and dialyzed in the buffer containing 50 mM morpholinopropanesulfonic acid (hereinafter referred to as "MOPS"), 10 mM $CaCl_2$ and 1 mM $NaN_3$. The resultant was used as a crude enzyme solution hereinafter. The protein concentration in the prepared crude enzyme solution was 2 mg/ml.

To 5 ml of the crude enzyme solution, 1 g of rice straw or chaff was added as a substrate, the mixtures were allowed to react at a temperature shown in both Table 1 and Table 2, for 72 hours or a week, respectively. Centrifugation of each resultant (3500 rpm, 2000×g, 15 minutes) was carried out after the reaction, the resulting precipitation was washed three times by adding sterilized water to it and centrifuging the resultant in a centrifuge (a trade name: KN-70, made by KUBOTA CORPORATION) (3500 rpm, 15 minutes), and then the weight of the resulting precipitation was measured in a balance after freeze-drying it. Removal ratio was a percentage that a weight obtained by deducting a weight of resultant from the initial weight accounts for, based on the initial weight. The results were shown in Table 1 and Table 2.

TABLE 1

|  | 20° C. | 30° C. | 40° C. | 50° C. |
| --- | --- | --- | --- | --- |
| Decomposed ratio of rice straw after 72-hour reaction (%) | 5.7 | 8.0 | 12.2 | 18.1 |
| Decomposed ratio of rice straw after one-week reaction (%) | 9.8 | 14.5 | 22.1 | 32.1 |

TABLE 2

|  | 20° C. | 30° C. | 40° C. | 50° C. |
| --- | --- | --- | --- | --- |
| Decomposed ratio of chaff after 72-hour reaction (%) | 3.5 | 5.8 | 7.6 | 11.3 |
| Decomposed ratio of chaff after one-week reaction (%) | 9.7 | 13.8 | 21.8 | 18.2 |

EXAMPLE 2

Chaff was added at 1% as a substrate to 50 mM MOPS buffer (pH 7.0) containing 10 mM $CaCl_2$ and 1 mM $NaN_3$ to prepare 50 ml of the mixture in total. To the mixture was added the crude enzyme solution of K32A obtained in EXAMPLE 1 which contained 1 mg of the proteins, and then the resultant was incubated at 50° C. for 24 hours. Centrifugation of the resultant was carried out after the incubation, the precipitating fraction was freeze-dried, and then the dry weight of the resultant was compared with that of the control group (no crude enzyme solution was added). As a result, each weight of the resultants treated with the crude enzyme solution was less than those of the control group by 30% to 32%. In addition, when the mixture was observed before centrifugation, it is observed visually that part of chaff was dissolved.

EXAMPLE 3

Two hundred fifty milliliters of ⅕ PTY culture medium added avicel at 0.1% which was treated with phosphoric acid was prepared under anaerobic condition, a single colony of *Clostridium cellulovorans* (ATCC 35296) was inoculated thereto, and a cultivation was carried out by shake culture at 37° C. for 72 hours (250 rpm, the amplitude of 10 mm). After the cultivation, the resulting supernatant of the culture was obtained by centrifugation (6000 rpm, 10 minutes). The supernatant was then sterilized by filtering it, and proteins in the supernatant were precipitated by adding ammonium sulfate to saturation (80%). The precipitated proteins were dissolved and dialyzed in 50 mM phosphate—12 mM citrate buffer. The resultant was used as a crude enzyme solution hereinafter. The protein concentration in the crude enzyme solution was adjusted to 2 mg/ml.

To 5 ml of the crude enzyme solution 1 g of rice straw or chaff was added as a substrate, the mixtures were allowed to react at a temperature shown in both Table 3 and Table 4, for 72 hours or a week, respectively. Centrifugation of each resultant (3500 rpm, 2000×g, 15 minutes) was carried out after the reaction, the resulting precipitation was washed three times by adding sterilized water to it and centrifuging the resultant in a centrifuge (a trade name: KN-70, made by KUBOTA CORPORATION) (3500 rpm, 15 minutes), and then the weight of the resulting precipitation was measured in a balance after freeze-drying it. Removal ratio was a percentage that a weight obtained by deducting a weight of resultant from the initial weight accounts for, based on the initial weight. The results were shown in Table 3 and Table 4.

TABLE 3

|  | 20° C. | 30° C. | 40° C. | 50° C. |
|---|---|---|---|---|
| Decomposed ratio of rice straw after 72-hour reaction (%) | 1.1 | 3.2 | 7.8 | 10.5 |
| Decomposed ratio of rice straw after one-week reaction (%) | 2.6 | 8.2 | 10.5 | 15.6 |

TABLE 4

|  | 20° C. | 30° C. | 40° C. | 50° C. |
|---|---|---|---|---|
| Decomposed ratio of chaff after 72-hour reaction (%) | 0.1 | 1.2 | 2.8 | 6.5 |
| Decomposed ratio of chaff after one-week reaction (%) | 1.2 | 2.0 | 5.6 | 8.8 |

INDUSTRIAL APPLICABILITY

The present invention provides a beneficial process for treating vegetable waste materials which needs less labor than labor required in previous processes. According to the present invention, vegetable waste materials can be allowed to be treated outside, for example, on the fields. According to the present invention, solved are problems such as the problem of treatment costs, the problem of energy, an environmental problem and the problem of time for treatment which are difficult to be solved by prior art, and it is possible to treat vegetable waste materials without depending on living conditions of microorganisms.

The invention claimed is:

1. An agent for decomposing plant fibrous materials in the field, which contains plant fibrous materials decomposing enzymes derived from a mesophile, and does not contain microorganism,
    in which the mesophile belongs to *Cellulomonas* sp.K32A strain (FERM BP-6766).

2. A process for treating vegetable waste materials comprising:
    cultivating a mesophile belonging to *Cellulomonas* sp.K32A strain (FERM BP-6766);
    obtaining enzymes from the mesophile;
    preparing an agent containing the enzymes derived from the mesophile, and not containing the microorganism;
    scattering the agent over vegetable waste material in a field; and
    allowing the agent for decomposing plant fibrous materials to act on a vegetable waste material left in the field.

3. A process according to claim 2, wherein said vegetable waste material is a member selected from the group consisting of rice, straw, chaff, straw, bagasse, vine of potato, fallen leaves and chips of wood.

4. A process according to claim 2, wherein said vegetable waste material is crushed into pieces before the agent is allowed to act on it.

5. A process according to claim 2 where allowing the agent to act on vegetable waste material is performed under the temperature condition of 20° C. to 50° C.

* * * * *